United States Patent [19]
Sammes et al.

[11] 3,951,956
[45] Apr. 20, 1976

[54] PROCESS FOR THE PREPARATION OF 3-HYDROXY PENAM-1-OXIDES AND DERIVATIVES THEREOF

[75] Inventors: Peter George Sammes, Sandy; Ian Harold Coates, London, both of England

[73] Assignee: Glaxo Laboratories Limited, Greenford, England

[22] Filed: Jan. 16, 1974

[21] Appl. No.: 433,714

[30] Foreign Application Priority Data
Jan. 17, 1973 United Kingdom............... 2524/73

[52] U.S. Cl............................. 260/239.1; 424/271; 260/243 C
[51] Int. Cl.²..................................... C07D 499/08
[58] Field of Search..................... 260/239.1, 243 C

[56] References Cited
UNITED STATES PATENTS
3,668,201  6/1972  Gutowski........................ 260/239.1
3,668,202  6/1972  Foster et al...................... 260/239.1

Primary Examiner—Nicholas S. Rizzo
Attorney, Agent, or Firm—Bacon & Thomas

[57] ABSTRACT

The invention relates to a novel process for the preparation of 3-hydroxy penam-1-oxides and esterified and etherified derivatives thereof. The process involves reaction of a penam-1-oxide mixed anhydride with a peracid followed by rearrangement and decarboxylation of the product initially formed to yield a 3-aroyloxy-penam-1-oxide. The latter compound may if desired subsequently be subjected to reductive cleavage to yield a 3-hydroxy compound, such reductive cleavage conveniently being effected by means of zinc and an ammonium salt under neutral or acidic conditions. The compounds prepared by the process of this invention are useful as intermediates in the preparation of antibiotics.

14 Claims, No Drawings

PROCESS FOR THE PREPARATION OF 3-HYDROXY PENAM-1-OXIDES AND DERIVATIVES THEREOF

This invention relates to a novel process for the preparation of 3-hydroxypenam-1-oxides and esterified and etherified derivatives thereof.

Belgian Pat. No. 770727 describes inter alia, compounds of the general formula

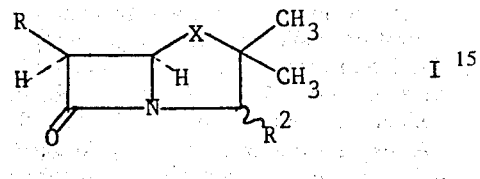

wherein R is a group $R^1CONH$ where $R^1CO$ represents an acyl group having from 1 to 21 carbon atoms, $R^2$ represents a hydroxyl or protected hydroxyl group and X represents SO in the α- or β-configuration. Such compounds are produced as intermediates in the conversion of penicillins to new ring structures. The compounds of formula I may, for example, be reacted to yield further intermediates such as the 4,7-diaza-6-oxo-2-thia-bicyclo[3,2,0]-hept-3-enes described in Belgian Pat. No. 770727. In addition to their use as intermediates, the compounds of formula I in general exhibit activity against parasites, e.g. worms, and in particular, the compound 1S,3S,5R,6R-2,2-dimethyl-3ξ-hydroxy-6-phenylacetylamidopenam-1-oxide has shown activity against *Nippostrongylus muris* and *Ascaridia galli*.

One method of preparing the compounds of formula I involves reacting a 3-isocyanato-penam of formula

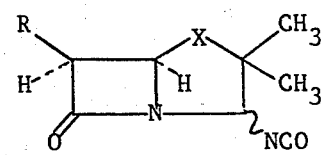

(wherein R and X are as hereinbefore defined) with an aqueous acid, as described in Belgian Pat. No. 770727. Compounds of formula II may be obtained by conversion of a penicillanic acid or its corresponding sulphoxide into an acid azide followed by rearrangement, i.e. a Curtius rearrangement reaction. However, large-scale reactions involving the Curtius rearrangement are potentially hazardous and may give rise to by-products such as ureas and thus an alternative route to the compounds of formula I is desirable.

The present invention is based on the discovery that compounds of formula I wherein R is a blocked amino group (which may for example be a group $R^1CONH$ as defined above) and $R^2$ represents an aroyloxy group may be prepared by the following reaction scheme:

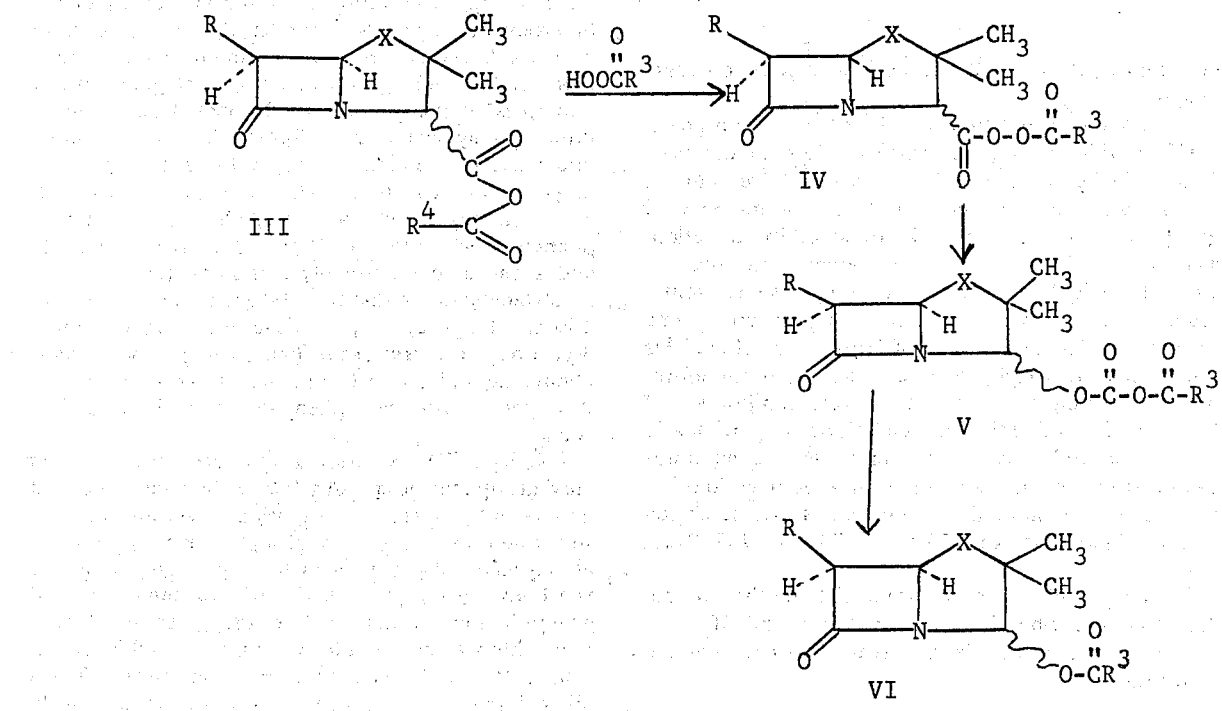

In the above reaction scheme, $R^4$ is an aliphatic or araliphatic group, $R^3$ is an aryl group and R and X are as hereinbefore defined. The substituent at the 3-position of the penam may be in either the α- or β-configuration but it is preferred that the said substituent be in the β-configuration.

According to the present invention, therefore, we provide a process for the preparation of compounds of the formula

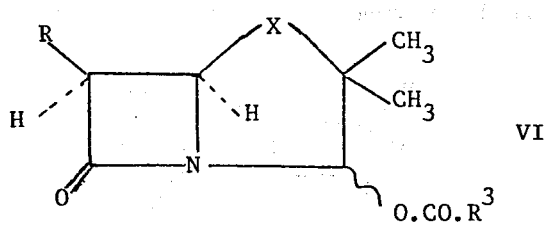

VI (wherein R represents a blocked amino group; R³ represents an aryl group; and X represents >SO in the α- or β-configuration) which comprises subjecting a compound of formula

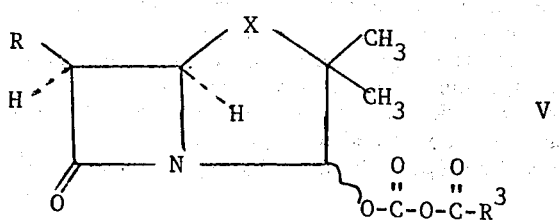

V (wherein R, R³ and X are as defined above) to decarboxylation.

Compounds of formula VI preferably carry a group O.COR³ which may be cleaved to yield compounds of formula I wherein R² is hydroxyl. We have found that it is particularly advantageous if R³ is an o-nitrophenyl group since this can readily be removed by reduction, as is described hereinafter. Compounds of formula I in which R² is hydroxyl may, if desired, be subsequently reacted with conventional esterifying or etherifying reagents to yield compounds of formula I in which R² is a protected hydroxyl group, as described in the aforementioned Belgian Patent. However, compounds of formula VI in which the ester OCOR³ is not particularly readily cleaved may be converted into compounds useful as intermediates in the synthesis of antibiotics, for example by methods analogous to those described in our Belgian Pats. Nos., 770726, 770729, 770730 and 770731.

The mixed anhydrides of formula III and their preparation are described in Belgian Pat. No. 750558.

The reaction of the mixed anhydride with the peracid of formula

HOOCR³ is conveniently effected in the presence of a solvent such as a chlorinated hydrocarbon, e.g. chloroform, preferably under anhydrous conditions, at low temperatures, e.g. temperatures of from −100° to +30°C, temperatures of about −70°C being preferred. The compound of formula IV obtained rearranges to a compound of formula V and on allowing the reaction mixture to stand or warm up, e.g. to room temperature, decarboxylation occurs to yield a compound of formula VI.

As stated hereinbefore, the compounds of formula VI in which R³ is an o-nitrophenyl group may be subjected to reductive cleavage to yield compounds of formula I wherein R² represents a hydroxyl group. The reductive cleavage is conveniently effected by means of a reagent capable of reducing a nitroaryl group to an N-hydroxylaminoaryl group.

Thus, for example, the reductive cleavage may be effected by means of zinc and an ammonium salt under neutral or acidic conditions e.g. zinc and ammonium chloride or ammonium acetate, preferably at temperatures of from −50° to +50°C. An aqueous reaction medium at about 0° is preferred.

As explained above, the group R may be a blocked amino group. As used herein, the term "blocked" means that the group which is blocked carries at least one substituent and is no longer a free amino, carboxyl or hydroxyl group. The term "protected" as used herein means that the group concerned carries at least one substituent which can be removed selectively without undue damage to the rest of the molecule, e.g. by hydrolysis, hydrogenolysis or reduction.

In general the following main classes are especially suitable for the acyl group R¹CO:

i. $R^u C_n H_{2n}$—CO where $R^u$ is an aryl (carbocyclic or heterocyclic), cycloalkyl, substituted aryl, substituted cycloalkyl, cyclohexadienyl or non-aromatic or mesoionic heterocyclic group, and $n$ is an integer from 1-4. Examples of this group include phenylacetyl; substituted phenylacetyl e.g. fluorophenylacetyl, nitrophenylacetyl, aminophenylacetyl, acetoxyphenylacetyl, methoxyphenylacetyl, methylphenylacetyl, or hydroxyphenylacetyl; N,N-bis(2-chloroethyl) aminophenylpropionyl; thienyl-2- and -3-acetyl; 4-isoxazolyl and substituted 4-isoxazolylacetyl; pyridylacetyl; tetrazolylacetyl or a sydnoneacetyl group. The substituted 4-isoxazolyl group may be a 3-aryl-5-methyl isoxazol-4-yl group, the aryl group being e.g. phenyl or halophenyl e.g. chloro- or bromophenyl. An acyl group of this type is 3-o-chlorophenyl-5-methyl isoxazol-4-yl-acetyl.

ii. $C_n H_{2n+1}$CO— where $n$ is an integer from 1-7. The alkyl group may be straight or branched and, if desired, may be interrupted by an oxygen or sulphur atom or substituted by e.g. a cyano group, a carboxy group, an alkoxycarbonyl group, a hydroxy group or a carboxycarbonyl group (—CO.COOH). Examples of such groups include cyanoacetyl, hexanoyl, heptanoyl, octanoyl, chloroacetyl, trichloroacetyl and butylthioacetyl.

iii. $C_n H_{2n-1}$CO— where n is an integer from 2-7. The alkenyl group may be straight or branched and, if desired, may be interrupted by an oxygen or a sulphur atom. An example of such a group is allylthioacetyl.

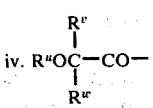

where $R^u$ has the meaning defined under (i) and in addition may be benzyl, and $R^v$ and $R^w$ which may be the same or different each represent hydrogen, phenyl, benzyl, phenethyl or lower alkyl. Examples of such groups include phenoxyacetyl, 2-phenoxy-2-phenylacetyl, 2-phenoxypropionyl, 2-phenoxybutyryl, 2-methyl-2-phenoxypropionyl, p-cresoxyacetyl and p-methylthiophenoxyacetyl.

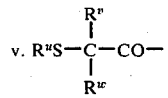

where $R^u$ has the meaning defined under (i) and, in addition, may be benzyl and $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

vi. $R^u Z(CH_2)_m CO-$ where $R^u$ has the meaning defined under (i) and, in addition, may be benzyl, Z is an oxygen or sulphur atom and $m$ is an integer from 2–5. An example of such a group is S-benzylthiopropionyl.

vii. $R^u CO-$ wherein $R^u$ has the meaning defined under (i). Examples of such groups include benzoyl, substituted benzoyl (e.g. aminobenzoyl), 4-isoxazolyl- and substituted 4-isoxazolyl carbonyl, cyclopentanecarbonyl, sydnonecarbonyl, naphthoyl and substituted naphthoyl (e.g. 2-ethoxynaphthoyl) quinoxalinylcarbonyl and substituted quinoxalinylcarbonyl (e.g. 3-carboxy-2-quinoxalinylcarbonyl). Other possible substituents for the benzoyl include alkyl, alkoxy, phenyl, phenyl substituted by carboxy, alkylamido, cycloalkylamido, allylamido, phenyl (lower) alkyl amido, morpholinocarbonyl, pyrrolidinocarbonyl, piperidinocarbonyl, tetrahydropyridino, furfurylamido or N-alkyl-N-anilino, or derivatives thereof and such substituents may be in the 2- or 2- and 6- positions. Examples of such substituted benzoyl groups are 2,6-dimethoxybenzoyl, 2-methylamidobenzoyl and 2-carboxybenzoyl. Where the group $R^u$ represents a substituted 4-isoxazolyl group, the substituents may be set out as above under (i). Examples of such 4-isoxazolyl groups are 3-phenyl-5-methylisoxazol-4-yl carbonyl, 3-o-chlorophenyl-5-methyl isoxazol-4-yl carbonyl and 3-(2,6-dichlorophenyl)-5-methyl-isoxazol-4-yl carbonyl.

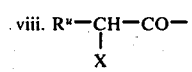

where $R^u$ has the meaning defined under (i) and X is amino, substituted amino (e.g. acylamido or a group obtained by reacting the α-aminoacylamido group of the 6-side chain with an aldehyde or ketone e.g. acetone, methylethylketone or ethyl acetoacetate), hydroxy, carboxy, esterified carboxy, triazolyl, tetrazolyl, cyano, halogeno, acyloxy (e.g. formyloxy or lower alkanoyloxy) or etherified hydroxy group. Examples of such acyl groups are α-aminophenylacetyl and α-carboxyphenylacetyl.

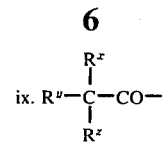

where $R^x$, $R^y$ and $R^z$ which may be the same or different may each represent lower alkyl, phenyl, or substituted phenyl and $R^x$ can also be hydrogen. An example of such an acyl group is triphenylmethylcarbonyl.

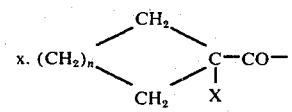

where X has the meaning defined under (viii) above and n is an integer of from 1 to 4. An example of such an acyl group is 1-aminocyclohexane-carbonyl.

xi. Amino acyl, for example $R^w CH(NH_2).(CH_2)_n CO$ where $n$ is an integer fom 1–10, or $NH_2.C_n H_{2n} Ar(CH_2)_m CO$, where $m$ is zero or an integer from 1–10, and $n$ is 0, 1 or 2, $R^w$ is a hydrogen atom or an alkyl, aralkyl or carboxy group or a group as defined under $R^u$ above, and Ar is an arylene group, e.g. p-phenylene or 1,4-naphthylene. Examples of such groups are disclosed in British Pat. Specification No. 1,054,806. A group of this type is the p-aminophenylacetyl group. Other acyl groups of this type include those, e.g. δ-aminoadipoyl, derived from naturally occurring amino acids and derivatives thereof e.g. N-benzoyl-δ-aminoadipoyl or N-chloroacetyl-δ-aminoadipoyl.

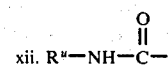

where $R^u$ has the meaning defined under (i) and in addition may be hydrogen, lower alkyl or halogen substituted lower alkyl. An example of such a group is $Cl(CH_2)_2 NHCO$.

Xiii. Substituted glyoxylyl groups of the formula $R^y.CO.CO-$ where $R^y$ is an aliphatic, araliphatic or aromatic group, e.g. a thienyl group, a phenyl group or a mono-, di- or tri-substituted phenyl group, the substituents being, for example, one or more halogen atoms (F, Cl, Br or I), methoxy groups, methyl groups or amino groups or a fused benzene ring. Included in this group are also the α-carbonyl derivatives of the above substituted glyoxylyl groups, formed for example with hydroxylamino, semicarbazide, thiosemicarbazide, isoniazide or hydrazine.

xiv. Formyl or haloformyl, e.g. chloroformyl.

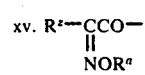

(having syn or anti configuration) wherein $R^z$ is a cyano group or a substituted or unsubstituted aryl (carbocyclic or heterocyclic) group or a cycloalkadienyl group and $R^a$ is
  a. hydrogen; or
  b. carboxylic acyl e.g. an aliphatic, cycloaliphatic or aromatic acyl group, or an acyl group in which the carbonyl group is linked to an aliphatic, cycloaliphatic or aromatic group through an oxygen or sulphur atom or through an imino group. Representative of such groups are alkanoyl, alkenoyl, alkynoyl, alkoxycarbonyl, alkylthiocarbonyl, aralkoxycarbonyl, aroyl, carbamoyl and thiocarbamoyl groups, all of which may carry substituents; or
  c. a monovalent organic group linked to the oxygen atom through a carbon atom e.g. a lower alkyl group, an alkenyl group, an alkynyl group, a cycloalkyl group, a cycloalkenyl group, a carbocyclic or heterocyclic aryl lower alkyl group, a carbocyclic aryl group or a heterocyclic aryl group, all of which may carry substituents.

Examples of groups $R^z$ include phenyl, naphthyl, thienyl, furyl, pyridyl, oxadiazolyl and isoxazolyl and substituted derivatives thereof carrying, for example, one or more hydroxy, halogeno (Cl,F or Br), amino, nitro, alkyl, alkoxy, phenyl or halophenyl atoms or groups.

Preferred amino protecting groups are the hydrocarbyloxycarbonyl groups (wherein the amino group forms part of a urethane), in particular alkoxycarbonyl groups such as methoxycarbonyl, ethoxycarbonyl and, most preferably, t-butoxycarbonyl groups, which may carry substituents such as halogen atoms as in the 2,2,2-trichloroethoxycarbonyl group, as well as aralkoxycarbonyl groups such as benzyloxycarbonyl, p-methoxybenzyloxycarbonyl and diphenylmethoxycarbonyl groups. Cycloalkoxycarbonyl groups are also advantageous, especially the adamantyloxycarbonyl group. The p-nitrobenzyloxycarbonyl group, which can be selectively removed by reduction, e.g. hydrogenolysis, is also useful. The initial penicillins carrying protecting groups of this type may be prepared from 6-aminopenams by conventional methods for example by reaction with an appropriate haloformic ester.

The group $R^3$ may be defined generally as an aryl group and may, for example, be a phenyl group or more preferably a substituted phenyl group. Suitable substituted phenyl groups include, in particular those in which the substituent enhances the electron-withdrawing properties of the phenyl group, for example, a halogen atom, e.g. a chlorine atom, in the meta-position, or a nitro group in the o and/or p-positions.

For a better understanding of the present invention, the following Examples are given by way of illustration only.

I.r. spectra were recorded with a Unicam SP200 spectrometer for Nujol mulls, unless otherwise stated, and u.v. spectra with a Unicam SP 800 spectrometer for ethanolic solutions. Mass spectra were determined with an A.E.I. MS9machine. $^1$H N.m.r. spectra were recorded with either a Varian T60 or HA 100 instrument for solutions in deuteriochloroform containing tetramethylsilane as internal reference. Reactions were monitored by t.l.c. on Merck silica gel $GF_{254}$ with ethyl acetate-benzene as solvents. M.p.s were determined with a Kofler hot-stage apparatus. Solutions were dried over anhydrous sodium sulphate.

EXAMPLE 1 a.

(1S,3S,5R,6R)-2,2-Dimethyl-6-phenylacetamidopenam-3-yl 3'-Chlorobenzoate 1-oxide (1S,5R,6R)-2,2-Dimethyl-6-phenylacetamidopenam-3-carboxylic acid 1-oxide (3.50 g) was suspended in dry chloroform (40 ml) and triethylamine (1.02 g) at −20°C with stirring whilst adding ethyl chloroformate (1.09 g). After 2 hours at −20°C the solution was cooled to −70°C and a solution of 3-chloroperbenzoic acid (85%; 2.8 g) in dry chloroform (20 ml) added over 1 hour. After addition, the reaction mixture was slowly allowed to warm to room temperature during 16 hours. The solution was then washed with aqueous sodium hydrogen carbonate (saturated; 2 × 20 ml), 2N-phosphoric acid (2 × 20 ml) and water. After drying, evaporation afforded a white foam (3.74 g; 82%). Purification by preparative t.l.c. gave the 3-chlorobenzoate (3.0 g; 65%) as a colourless foam $[\alpha]_D^{24}$ + 100.5° (c 1.2, $CHCl_3$), $\nu$max. 3400, 1800, 1735, 1680, 1500 and 1510 $cm^{-1}$, $\tau$ 2.90 (10 Hm, aromatic protons and amide NH) 3.40 (1Hs, 3-H), 4.05 (1Hdd, J 4, 11 Hz, 6-H), 4.90 (1Hd, J 4 Hz, 5-H), 6.42 (2Hs, $PhCH_2$), 8.39 (3Hs), 8.60 (3Hs). Found: C, 57.3; H, 4.5; Cl, 7.65; N, 5.8; S, 6.9. $C_{22}H_{21}Cl N_2O_5S$ requires C, 57.3; H, 4.6; Cl, 7.7; N, 6.1;S, 6.95%).

EXAMPLE 2

(1S,3S,5R,6R)-2,2-Dimethyl-6-phenylacetamidopenam-3-yl-2'-Nitrobenzoate-1-oxide

2-Nitroperbenzoic acid (98%; 2.2 g) in THF (40 ml) was added to a solution of the mixed anhydride (3.5 g) prepared as in Example 1(a) at −70°. After allowing the reaction mixture to warm to room temperature overnight the product was isolated in the usual way. Evaporation of the chloroform extract afforded an amorphous foam which was crystallised from methanol as needles of the 2-nitrobenzoate (3.8 g; 80%) m.p. 148.5°–149°, $[\alpha]_D^{30}$ + 181° (c 0.87, $CHCl_3$) $\nu$max. 3300, 1800, 1740, 1685 $cm^{-1}$, $\tau$ 2.00 − 2.50 (4H, m, o-$NO_2C_6H_4$), 2.69 (5H, Ph) 2.90 (1H, NH), 3.42 (1H, s, 3-H), 4.00 (1H, dd, J 4, 10 Hz, 6-H) 4.95 (1H, d, J 4 Hz, 5-H) 6.40 (2H, s, $PhCH_2$), 8.32 (3H, s) 8.70 (3H, s). (Found: C, 55.85; H, 4.6; H, 9.15; S, 6.9. $C_{22}H_{21}N_3O_7S$ requires C, 56.0; H, 4.5; N, 8.9; S, 6.8%).

EXAMPLE 3

(1S,3S,5R6R)-2,2-Dimethyl-6-phenylacetamidopenam-3-yl-4'-Nitrobenzoate-1-oxide

This was prepared in a similar manner to the 2-nitrobenzoate (see Example 2). The mixed anhydride (from 3.5 g acid sulphoxide) with 4-nitroperbenzoic acid (90%, 2.4 g) afforded the title ester (3.1 g; 65%) as a non-crystalline foam $[\alpha]_D^{23}$ + 135° (C 0.85, $CHCl_3$) $\nu$ max. ($CHCl_3$) 3400, 1795, 1730, 1680, 1540, and 1360 $cm^{-1}$, $\tau$ 1.75 (4H, m, p-$NO_2C_6H_4$) 2.70 (6H, m, Ph and NH), 3.35 (1H, s, 3-H), 3.99 (1H, dd, J 4, 10 Hz, 6-H), 4.85 (1Hd, J 4 Hz, 5-H), 6.4 (2H, s, $PhCH_2$), 8.32 (3H, s), 8.52 (3H, s). Found: C, 56.5; H, 4.8; N, 8.8; S, 6.9. $C_{22}H_{21}N_3O_7S$ requires C, 56.0; H, 4.5; N, 8.9; S, 6.8%).

EXAMPLE 4

(1S,3S,5R,6R)-2,2-Dimethyl-6-phenylacetamidopenam-3-yl-2',4'-Dinitrobenzoate 1-oxide (1S,3S,5R,6R)-2,2-dimethyl-3-hydroxy-6-phenyl acetamidopenam-1-oxide (1.0 g) in anhydrous THF (10 ml) was treated with 2,4-dinitrobenzoyl chloride (3 equiv.) in benzene (15 ml) containing pyridine (1.0 ml) at 0°C. After allowing the reaction mixture to warm to room temperature for 15 hours, it was poured into water and extracted with ethyl acetate. The organic layer was washed with aqueous sodium carbonate (3% w/v, 2 × 20 ml), 2N-phosphoric acid (2 × 20 ml) and water (20 ml) before drying and evaporation. The resultant foam crystallised from methanol to give the 2,4-dinitrobenzoate (0.95 g, 60%), m.p. 160°–161°, $[\alpha]_D^{29}$ + 161.5° (c 0.89, CHCl$_3$), $\nu$ max. 3400, 1800, 1740, 1680, 1540 and 1360 cm$^{-1}$ $\tau$ 1.1–2.1 (3H, m, aromatic), 2.70 (5Hm, Ph), 2.90 (1H, broadened d, NH), 3.40 (1H, s, 3-H), 3.98 (1H, dd, J 4, 10 Hz, 6-H), 4.90 (1H, d, J 4 Hz, 5H), 6.40 (2H, s, CH$_2$ Ph), 8.35 (3H, s), and 8.73 (3H, s). Found: C, 50.9; H, 4.0; N, 10.45; S, 6.4. C$_{22}$H$_{20}$N$_4$O$_9$S requires, C, 51.2; H, 3.9; N, 10.8; S, 6.2%).

EXAMPLE 5

Reduction of (1S,3S,5R,6R)-2,2-dimethyl-6-phenylacetamidopenam-3-yl-2'-nitrobenzoate 1-oxide The general procedure was as follows. The 2'-nitrobenzoate (1 equiv.) in THF at 0° was stirred with ammonium chloride (7 equiv.) in water, the volume of solvent being adjusted to give a homogeneous solution. Zinc dust (2.1 equiv.) was added slowly, in portions, to the vigorously stirred reaction mixture. The reactions were monitored by t.l.c. After disappearance of the starting material (0.5–2 hours) the reaction mixture was filtered and the solids washed with ethyl acetate and water. The filtrate was extracted with ethyl acetate, washing out the benzo[d]isoxazolinone with aqueous sodium hydrogen carbonate solution. The extract was dried and evaporated to give the alcohol, (1S,3S,5R,6R)-2,2-dimethyl-3-hydroxy-6-phenylacetamidopenam-1-oxide, in essentially quantitative yield. Ammonium acetate could also be used in place of the chloride.

We claim:

1. A process for the preparation of compounds of the formula

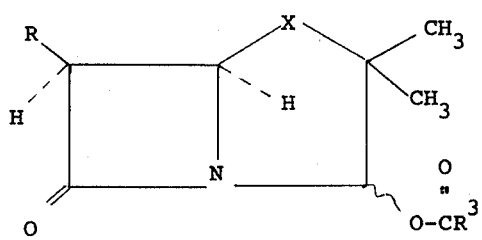

VI wherein R represents a blocked amino group; R$^3$ represents phenyl or phenyl substituted with a substituent which enhances the electron withdrawing properties of the phenyl group; and X represents >SO in the α- or β-configuration; which comprises subjecting a compound of formula

V wherein R, R$^3$ and X are as defined above, to decarboxylation.

2. A process as claimed in claim 1 wherein the compound of formula V is obtained by reacting a compound of formula

III wherein R and X are as defined in claim 1 and R$^4$ represents an aliphatic or araliphatic group with a peracid of formula

HOOCR$^3$ wherein R$^3$ is as defined in claim 1, the compound of formula

IV initially obtained rearranging to yield the required compound of formula V.

3. A process as claimed in claim 2 wherein the reaction of the compound of formula III with the peracid is effected at a temperature of from −100° to +30°C.

4. A process as claimed in claim 1 in which a compound of formula VI is subsequently subjected to cleavage to replace the group —COR³ by hydrogen.

5. A process as claimed in claim 4 wherein R³ is an o-nitrophenyl group and the cleavage is effected by means of zinc and an ammonium salt under neutral or acidic conditions.

6. A process as claimed in claim 5 wherein the reductive cleavage is effected at a temperature of from −50° to +50°C.

7. A process as claimed in claim 1 wherein R represents a group R¹CONH where R¹CO is an acyl group containing 1 to 21 carbon atoms.

8. A process as claimed in claim 4 wherein the 3-hydroxy compound obtained by replacing —CO.R³ by hydrogen is subsequently reacted with an esterifying or etherifying reagent to yield a corresponding protected hydroxyl derivative.

9. A process as claimed in claim 1 wherein the group R³ is phenyl or phenyl substituted with a substituent which enhances the electron withdrawing properties of the phenyl group.

10. A process as claimed in claim 1 wherein the decarboxylation is effected by allowing the compound of formula V to stand or warm up to room temperature.

11. A process as claimed in claim 2 wherein a compound of formula 3 is reacted with the peracid in the presence of a solvent and at a temperature of from −100° to +30°C.

12. A method as claimed in claim 9 wherein the substituent which enhances the electron withdrawing properties of the phenyl group is a halogen substituted in the meta position or a nitro group substituted in the ortho or para positions.

13. A process as claimed in claim 11 wherein the solvent is a chlorinated hydrocarbon and the reaction with the peracid is effected under anhydrous conditions.

14. A process as claimed in claim 2 wherein R⁴ is ethoxy.

* * * * *